United States Patent
Mueller

(10) Patent No.: US 12,091,646 B2
(45) Date of Patent: Sep. 17, 2024

(54) METHODS FOR MOISTURE REMOVAL AND PEST CONTROL OF GRAINS

(71) Applicant: Fermentation Technology Services LLC, Chicago, IL (US)

(72) Inventor: Steffen Mueller, Chicago, IL (US)

(73) Assignee: FERMENTATION TECHNOLOGY SERVICES, Chicago, IL (US)

( * ) Notice: Subject to any disclaimer, the term of this patent is extended or adjusted under 35 U.S.C. 154(b) by 0 days.

(21) Appl. No.: 18/171,326

(22) Filed: Feb. 17, 2023

(65) Prior Publication Data

US 2024/0150689 A1    May 9, 2024

Related U.S. Application Data

(60) Provisional application No. 63/422,573, filed on Nov. 4, 2022.

(51) Int. Cl.
| | |
|---|---|
| *C12F 3/02* | (2006.01) |
| *A01N 59/04* | (2006.01) |
| *A23K 10/38* | (2016.01) |
| *C12C 1/02* | (2006.01) |
| *C12C 1/067* | (2006.01) |
| *C12C 1/073* | (2006.01) |
| *C12M 1/16* | (2006.01) |

(52) U.S. Cl.
CPC .............. *C12F 3/02* (2013.01); *A01N 59/04* (2013.01); *A23K 10/38* (2016.05); *C12C 1/02* (2013.01); *C12C 1/067* (2013.01); *C12C 1/073* (2013.01); *C12M 21/16* (2013.01)

(58) Field of Classification Search
CPC ............ A23K 10/38; C12F 3/02; C12C 1/073
See application file for complete search history.

(56) References Cited

U.S. PATENT DOCUMENTS

| | | | | |
|---|---|---|---|---|
| 4,699,642 A | * | 10/1987 | Perry ...................... | F25J 1/0027 62/928 |
| 5,425,929 A | * | 6/1995 | van Oeveren ............ | C12F 3/02 423/437.1 |
| 6,167,636 B1 | * | 1/2001 | Kepplinger ............... | F23G 5/46 34/381 |

(Continued)

FOREIGN PATENT DOCUMENTS

| | | | |
|---|---|---|---|
| CA | 2162096 A1 | * | 5/1996 |
| CN | 201067059 Y | * | 6/2008 |

(Continued)

OTHER PUBLICATIONS

DE 10 2020 208 021 A1 (Buchhauser, Ulrich) Dec. 30, 2021 [retrieved on Feb. 9, 2024]. Retrieved from Foreign Image and Text database, translation by Clarivate Analytics. (Year: 2021).*

(Continued)

*Primary Examiner* — John J Norton
(74) *Attorney, Agent, or Firm* — MCDONNELL BOEHNEN HULBERT & BERGHOFF, LLP

(57) ABSTRACT

The present disclosure provides methods for treating one or more grains in an ethanol plant or alcohol brewery, methods of drying, cooling, disease control of dried distillers grains with soluble (DDG), barley, or brewer's spent grain (BSG), and a system for treating one or more grains in an ethanol plant or alcohol brewery by these disclosed methods.

16 Claims, 2 Drawing Sheets

(56) References Cited

U.S. PATENT DOCUMENTS

| | | | | |
|---|---|---|---|---|
| 2004/0250682 A1* | 12/2004 | Martynowicz | ............. | F25J 3/08 |
| | | | | 96/306 |
| 2020/0332235 A1* | 10/2020 | Halter | ...................... | A01G 9/18 |
| 2024/0093382 A1* | 3/2024 | Carlson | ..................... | C12F 3/02 |

FOREIGN PATENT DOCUMENTS

| | | | | | |
|---|---|---|---|---|---|
| CN | 102047954 A | * | 5/2011 | | |
| CN | 106281823 A | * | 1/2017 | ............... | A23B 9/20 |
| CN | 106553844 A | * | 4/2017 | | |
| CN | 112841298 A | * | 5/2021 | | |
| DE | 102008039374 A1 | * | 2/2010 | ............. | C12C 7/163 |
| DE | 102012219964 A1 | * | 4/2014 | ............. | C12C 13/00 |
| DE | 102020208021 A1 | * | 12/2021 | | |
| EP | 1454881 A1 | * | 9/2004 | ............ | C01B 31/22 |
| EP | 2292726 A1 | * | 3/2011 | ........... | C12C 13/025 |
| FR | 3112085 A1 | * | 1/2022 | | |
| WO | WO-2011141106 A1 | * | 11/2011 | ............. | F23G 5/006 |

OTHER PUBLICATIONS

DE 10 2012 219 964 A1 (Gattermeyer, Peter et al.) Apr. 30, 2014 [retrieved on Feb. 9, 2024]. Retrieved from Foreign Image and Text database, translation by Clarivate Analytics. (Year: 2014).*

EP 2 292 726 A1 (Hertel, Marcus) Mar. 9, 2011 [retrieved on Feb. 9, 2024]. Retrieved from Foreign Image and Text database, translation by Clarivate Analytics. (Year: 2011).*

WO 2011/141106 A1 (Zobel, Karl et al.) Nov. 17, 2011 [retrieved on Feb. 9, 2024]. Retrieved from Foreign Image and Text database, translation by Clarivate Analytics. (Year: 2011).*

DE 10 2008 039 374 A1 (Hahn, Adolf) Feb. 25, 2010 [retrieved on Feb. 9, 2024]. Retrieved from Foreign Image and Text database, translation by Clarivate Analytics. (Year: 2010).*

* cited by examiner

METHODS FOR MOISTURE REMOVAL AND PEST CONTROL OF GRAINS

CROSS-REFERENCE TO RELATED APPLICATIONS

This application claims the benefit of priority to U.S. Provisional Application No. 63/422,573, filed on Nov. 4, 2022, which is incorporated herein by reference as if set forth in its entirety.

FIELD OF THE DISCLOSURE

The present disclosure provides and system and methods of grain treatment related to moisture removal and grain disease and pest control.

BACKGROUND

Grain quality control is an important aspect of alcohol fermentation plants. Growers, or grain elevators, delivering and selling their grain to ethanol plants must meet strict moisture and fungi control requirements in order to ensure safe grain storage onsite, as well as, precise controlled grain processing parameters.

Grain, dried distillers grain (DDG) and brewer's spent grain (BSG) and their storage facilities are subject to disease pressure, insect infestation, and mold (e.g. aflatoxin). The effects of climate change will increase these issues. Current methods of mitigating these issues involve harmful chemicals and high energy usage.

High moisture levels of grain can increase the risk of fungal formation at ethanol plant storage facilities. Fungi can not only deteriorate grain quality, but also transfer to DDG and BSG during the fermentation process and thereby pose a health risk to DDG- and BSG-consuming animal feedstock. DDG and BSG animal feed produced at the ethanol plant must meet FDA quality standards. On the back end of an ethanol plant, DDG and BSG can only be shipped if the product meets certain flowability requirements. Cooling the DDG and BSG after drying reduces the "curing" period instituted by ethanol plants between DDG and BSG drying and its shipment to improve flowability and reduce product shrinkage.

Currently, large fans and significant amounts of propane gas are being used each harvest season for grain drying on the grower side. Natural gas fired driers are used at ethanol plants to dry DDG and in some case BSG. Additionally, ethanol plants produce large amounts of carbon dioxide ($CO_2$) as a byproduct of the fermentation process and from natural gas combustion for thermal process energy generation. Most of the produced $CO_2$ is released into the atmosphere. Some of the $CO_2$ is recovered, compressed and liquefied for offsite shipment to merchant gas markets (beverage industry, animal processing facilities, and dry ice production) or for use in enhanced oil recovery. Several ethanol plants also compress and liquefy the $CO_2$ for permanent sequestration in geological formation. There is a worldwide effort to reduce greenhouse gases, and chemical and energy usage.

Thus, there is a need in the art for methods of recycling $CO_2$ produced by ethanol plants, and reducing the amount of energy required for drying and grain disease and pest control of the grain.

SUMMARY OF THE DISCLOSURE

Provided herein is a method of treating one or more grains in a plant, the method comprising releasing $CO_2$ in a grain storage facility, wherein the $CO_2$ is a byproduct of alcohol fermentation or thermal energy generation.

Also provided herein is a method of decreasing energy use in grain moisture removal, the method comprising treating a grain according to the method of treating one or more grains in a plant, the method comprising releasing $CO_2$ in a grain storage facility, wherein the $CO_2$ is a byproduct of alcohol fermentation or thermal energy generation.

Also provided herein is a system for treating one or more grains in a plant, the system comprising a control center, one or more ducts, and a $CO_2$ source.

Also provided herein is a method comprising providing an ethanol plant or alcohol brewery, providing an alcohol fermentation of grain facility on site at the ethanol plant or alcohol brewery, capturing $CO_2$ produced from the alcohol fermentation or thermal energy generation at the grain facility, providing a grain storage facility on site at the ethanol plant or alcohol brewery, and directing the $CO_2$ captured from alcohol fermentation or thermal energy generation of grain facility through grain stored in the grain storage facility, wherein the $CO_2$ directed through the grain serves to dry the grain stored in the grain storage facility, and wherein the $CO_2$ directed through the grain serves to provide disease control of the grain stored in the grain storage facility.

These and other features, objects, and advantages of the present disclosure will become better understood from the description that follows. In the description, reference is made to the accompanying drawings, which form a part hereof and in which there is shown by way of illustration, not limitation, embodiments of the disclosure. The description of preferred embodiments is not intended to limit the disclosure to cover all modifications, equivalents, and alternatives. Reference should therefore be made to the claims recited herein for interpreting the scope of the disclosure.

BRIEF DESCRIPTION OF THE DRAWINGS

The disclosure will be better understood, and features, aspects, and advantages other than those set forth above, will become apparent when consideration is given to the following detailed description thereof. Such detailed description refers to the following drawings.

DETAILED DESCRIPTION

Figure 1:
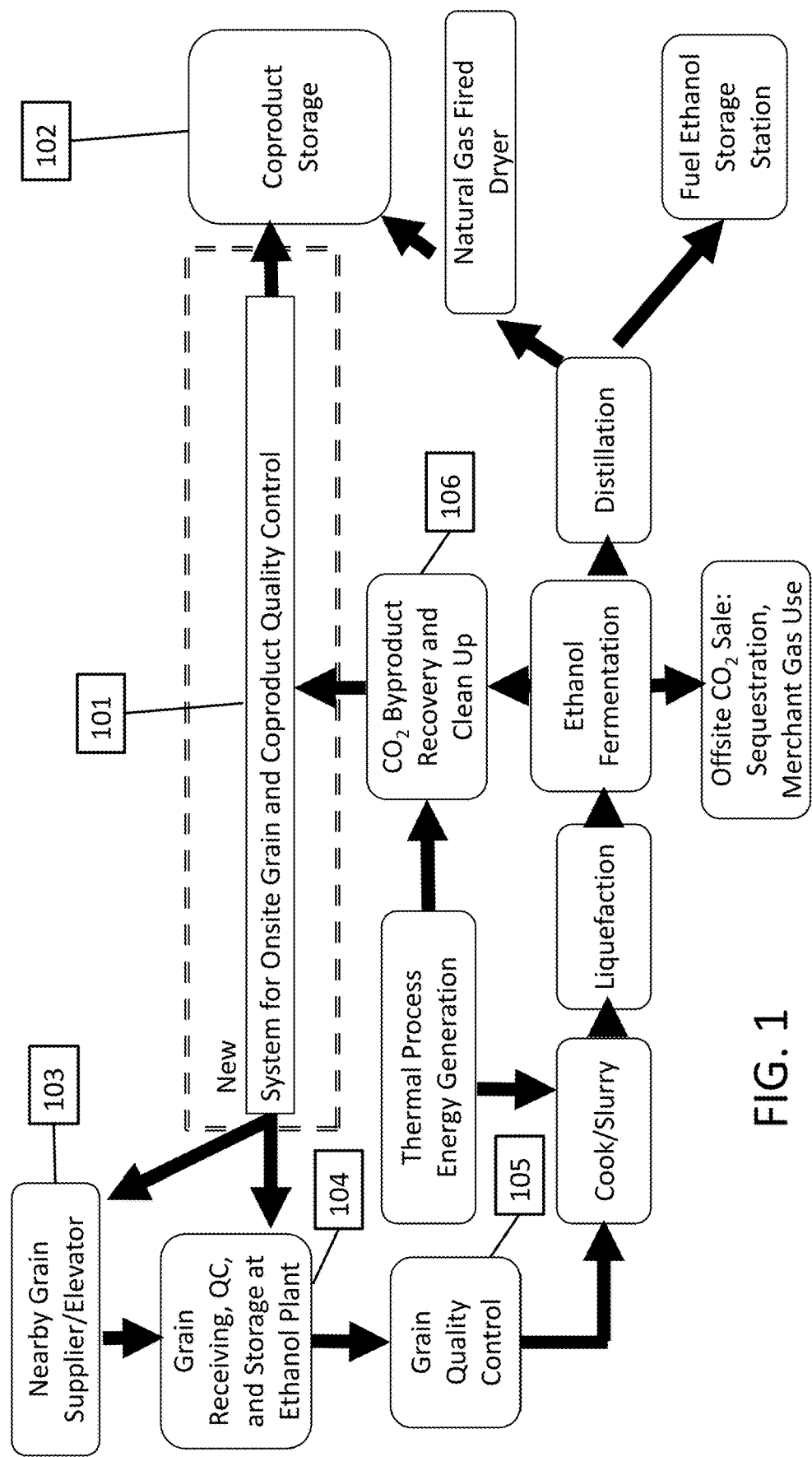
FIG. 1 shows a diagram of the integration of the disclosed method with an ethanol plant. The main system for onsite grain and coproduct quality control is housed at the ethanol plant (101). The system can be used for DDG and BSG drying, quality control, and storage maintenance (102). The onsite system can be used to treat nearby grain for grain suppliers (103), and grain receiving, quality control, and storage at an ethanol plant (104). The onsite system has downstream effects on grain quality control (105). Ethanol fermentation and thermal energy generation leads to $CO_2$ production and the $CO_2$ can be recovered onsite (106). The new system allows for onsite use of the recovered $CO_2$.

For the purposes of promoting an understanding of the principles of the disclosure, reference will now be made to embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Definitions

As used in the specification, articles "a" and "an" refer to one or to more than one (i.e., at least one) of the grammatical object of the article. By way of example, "an element" means at least one element and can include more than one element.

"About" is used to provide flexibility to a numerical range endpoint by providing that a given value can be "slightly above" or "slightly below" the endpoint without affecting the desired result. The term "about" in association with a numerical value means that the numerical value can vary by plus or minus 5% or less of the numerical value.

Throughout this specification, unless the context requires otherwise, the word "comprise" and "include" and variations thereof (e.g., "comprises," "comprising," "includes," "including") will be understood to imply the inclusion of a stated component, feature, element, or step or group of components, features, elements, or steps but not the exclusion of any other integer or step or group of integers or steps.

As used herein, "and/or" refers to and encompasses any and all possible combinations of one or more of the associated listed items, as well as the lack of combinations where interpreted in the alternative ("or").

Recitation of ranges of values herein are merely intended to serve as a succinct method of referring individually to each separate value falling within the range, unless otherwise indicated herein. Furthermore, each separate value is incorporated into the specification as if it were individually recited herein. For example, if a range is stated as 1 to 50, it is intended that values such as 2 to 4, 10 to 30, or 1 to 3, etc., are expressly enumerated in this disclosure. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by a person of ordinary skill in the art to which this disclosure belongs.

The term "grain", as used herein, refers to corn, barley, sorghum, or any suitable grain for ethanol production.

The term "dried distillers grain, sometimes also referred to as distillers dried grain, (DDG)", as used herein, refers to a coproduct of grain ethanol production. DDG is often used as protein-rich animal feed.

The term "brewer's spent grain, sometimes also referred to as spent grain, (BSG)", as used herein, refers to a coproduct of beer production. BSG is often used as animal feed.

DDG and BSG, as used herein, are referred to as coproducts.

The term "plant", as used herein, refers to an ethanol plant, or alcohol brewery. The size of corn ethanol plants, for example, in the United States ranges from approximately 50-300 million gallons per year of ethanol production. The median ethanol plant produces about 120 million gallons per year of ethanol, 300,000 tons of coproducts, and about 300,000 tons of fermentation carbon dioxide ($CO_2$). A plant of this size uses approximately 1 million metric tons of corn grain for alcohol production and 850,000 MMBtu (million British thermal units) to dry DDG.

The term "ambient temperature", as used herein, refers to $CO_2$ that is at the temperature of the process it is produced at, or at or near room temperature.

The term "treating", as used herein, refers to applying a treatment to a grain.

The term "plant pathogen", as used herein, refers to any insect, bacteria, fungus, or nematode capable of infecting a plant or grain with a disease.

Current technologies for reducing plant pathogens include spraying the storage facilities with harmful pesticide and insecticide chemicals, sourcing and transporting liquid $CO_2$ to the storage facility for controlled atmosphere treatment thereby incurring high transportation cost and transportation emissions, using electric grain chillers which incur the upstream emissions associated with electricity production, and using aeration fans which also require significant amounts of electricity.

The methods disclosed herein disclose configurations and new uses for the plant's fermentation and thermal energy generation $CO_2$ byproduct for moisture reduction and pest and fungal control. For instance, new uses for recovered fermentation $CO_2$ in the area of onsite grain and coproduct quality control provide two major applications: 1) moisture reduction via grain and coproduct drying and cooling, and 2) reduction in pesticide, insect, and fungi pressure on stored grain and coproducts via controlled $CO_2$ fumigation and $CO_2$ enriched aeration. Additionally, $CO_2$ that would otherwise be vented to the atmosphere as a greenhouse gas is repurposed for moisture removal and cooling grain and coproducts.

Furthermore, the disclosed methods provide operational benefits. Utilizing recovered $CO_2$ allows ethanol plants to accept incoming grain with larger variations in moisture, insect and mold pressure and ship coproducts with streamlined moisture removal operation, better flowability, reduced product shrinkage and lower fungi risk since the onsite treatment with $CO_2$ will enable a better control of these variables. Additionally, corn growers delivering to ethanol plants will be able to deliver corn at a higher moisture content, therefore saving drying time and expense as shown in Example 1.

The disclosed method utilizes the thermodynamic principle of the $CO_2$ refrigeration cycle for moisture removal via grain cooling with the $CO_2$ vaporized gas acting as the chilling medium. This is different from the current thermodynamic principle of drying grain with heat (e.g., corn drying in propane dryers, coproduct drying in natural gas fired dryers). With the methods disclosed herein, alcohol and ethanol plants, which have access to large quantities of $CO_2$ from the alcohol fermentation process, can utilize the $CO_2$ refrigeration cycle onsite for grain moisture removal.

In some embodiments, the method of treating one or more grains in a plant comprises releasing $CO_2$ in a grain storage facility, wherein the $CO_2$ is a byproduct of alcohol fermentation.

In some embodiments, the plant is an ethanol plant, or an alcohol brewery.

In some embodiments, the grain treatment drying, cooling, disease control, or combinations thereof.

In further embodiments, the treatment is drying, cooling, or combinations thereof.

In yet further embodiments, the treatment is disease and pest control.

In specific embodiments, $CO_2$ is a byproduct of alcohol fermentation.

In specific embodiments, $CO_2$ is a byproduct of thermal energy generation.

In specific embodiments, the $CO_2$ is captured $CO_2$ obtained onsite at the ethanol plant or alcohol brewery.

In some embodiments, the $CO_2$ is a compressed gas, a liquid, or at ambient temperature.

In some embodiments, the $CO_2$ is a compressed gas, or ambient temperature gas.

In further embodiments, the compressed gas, or ambient temperature gas, are used for disease control.

In some embodiments, the $CO_2$ is a liquid.

In further embodiments, the liquid is vaporized.

In some embodiments, the liquid, or ambient temperature gas, are used for drying, cooling, or combinations thereof.

In some embodiments, the grain is any consumable grain.

In further embodiments, the consumable grain is corn, dried distillers grain (DDG), barley, or brewer's spent grain (BSG).

In some embodiments, the method of decreasing grain drying time comprises treating a grain according to the method of treating one or more grains in a plant comprising releasing $CO_2$ in an onsite grain storage facility.

In some embodiments, fermentation $CO_2$ is directly used at ambient conditions for pest control. $CO_2$ is used as a fumigation agent wherein the mortality of insects in the stored grain is increased with high concentrations of $CO_2$ (60-70% concentration).

Current practices for fumigating grain at an ethanol plant includes pesticide use. However, pesticide fumigation is not an option for coproducts, as coproducts are used for animal feed. The methods disclosed herein ensure that coproducts can be fumigated.

In some embodiments, the drying energy is reduced by about 15% to about 25% but for corn grain delivered to an ethanol plant at just slightly elevated moisture levels, drying energy can be reduced by 50%.

In some embodiments, the method of disease control of a grain comprises treating the grain by releasing $CO_2$ in a grain storage facility, wherein the $CO_2$ is a byproduct.

In some embodiments, the disease is caused by a plant pathogen.

In some embodiments, the plant pathogen is a bacteria, fungus, or virus.

In further embodiments, the plant pathogen is a fungus. In certain embodiments, the fungus is an aflatoxin-producing fungus.

In some embodiments, a system for treating one or more grains in a plant comprises releasing $CO_2$ in a grain storage facility, wherein the system comprises a control center connected to a $CO_2$ pressure regulator, one or more fans, a $CO_2$ meter, and a vaporizer.

In some embodiments, the $CO_2$ pressure regulator is connected to the one or more ducts.

In further embodiments, the method decreases energy use during grain moisture removal when compared to traditional moisture removal methods.

In some embodiments, a method comprises providing an ethanol plant or alcohol brewery, providing an alcohol fermentation of grain facility on site at the ethanol plant or alcohol brewery, capturing $CO_2$ produced from the alcohol fermentation, or thermal energy generation, of the grain facility, providing a grain storage facility on site at the ethanol plant or alcohol brewery, directing the $CO_2$ captured from the alcohol fermentation of grain facility through grain stored in the grain storage facility.

In further embodiments, the method disclosed above comprises directing the $CO_2$ captured from the alcohol fermentation, or thermal energy generation, of the grain facility through grain stored in the grain storage facility, wherein the $CO_2$ directed through the grain serves to dry the grain stored in the grain storage facility, and wherein the $CO_2$ directed through the grain serves to provide disease control of the grain stored in the grain storage facility.

In some embodiments, the ratio of $CO_2$ directed through the grain in the grain storage facility to weight of grain in the grain storage facility is in the range of 1% to 3%.

In some embodiments, the weight of $CO_2$ directed through the grain in the grain storage facility to the weight of $CO_2$ emitted by the facility is in the range of 1% to 20%.

Various exemplary embodiments of compositions and methods according to this disclosure are now described in the following non-limiting Examples. The Examples are offered for illustrative purposes only and are not intended to limit the scope of the present disclosure in any way. Indeed, various modifications of the disclosure in addition to those shown and described herein will become apparent to those skilled in the art from the foregoing description and the following Examples and fall within the scope of the appended claims.

EXAMPLES

The Examples that follow are illustrative of specific embodiments of the disclosure, and various uses thereof. They are set forth for explanatory purposes only and should not be construed as limiting the scope of the disclosure in any way.

Example 1: Integration of Method in Ethanol Plant

Figure 2:
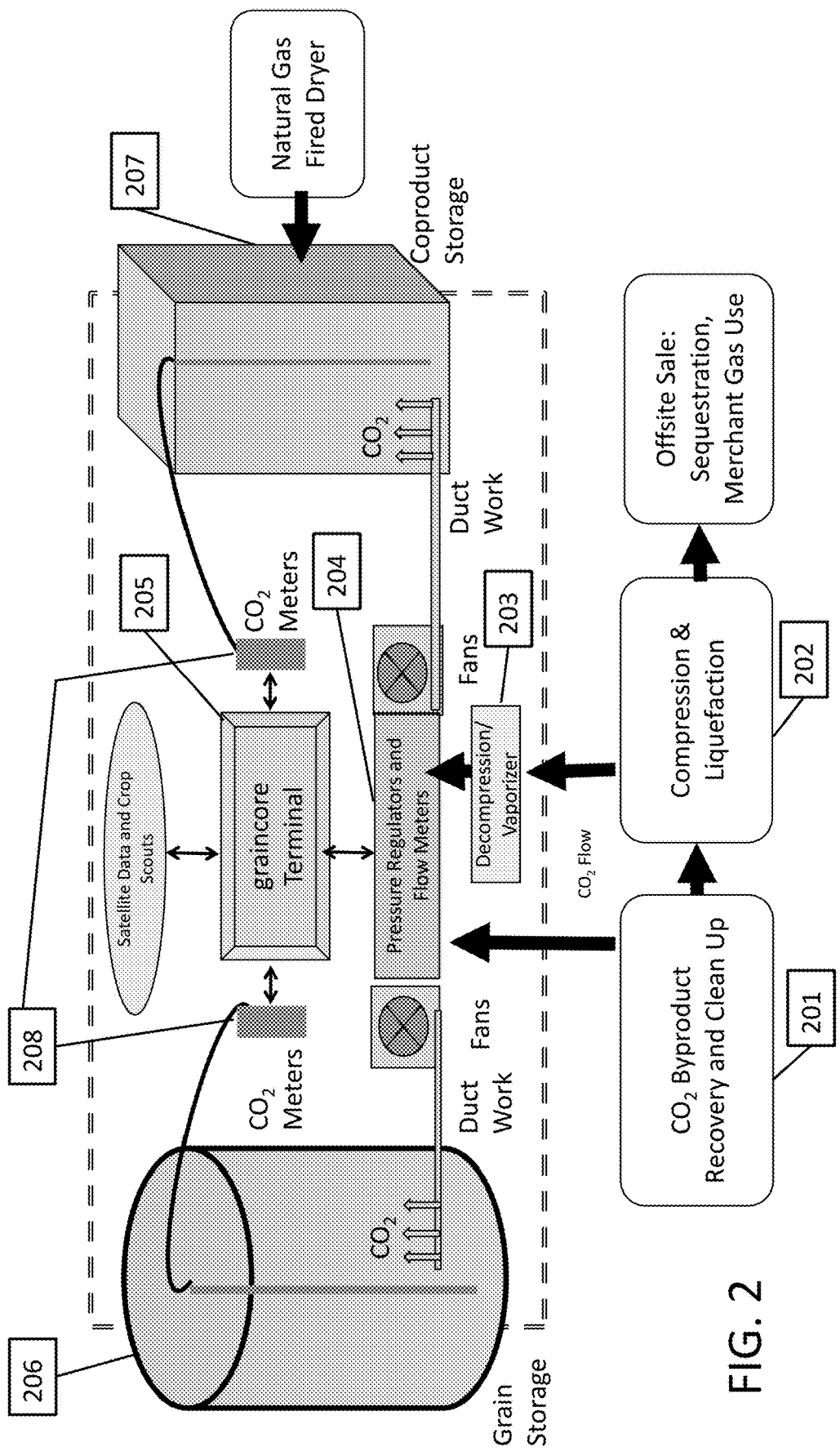
FIG. 2 shows a configuration of the disclosed system and method. Ethanol recovered from an ethanol fermentation or thermal energy generation at the grain facility can be used at ambient temperature (201) or compressed and liquified (202). Compressed $CO_2$ is vaporized prior to use (203). The recovered $CO_2$ (201 and 202) then passes through a pressure regulator and flow meter (204) that gives feedback to the grain $CO_2$ terminal "Control Center" (205). Fans blow the $CO_2$, entering through the pressure regulator, via duct work where $CO_2$ is then released to the grain storage (206) or DDG or BSG storage facilities (207) via duct work. $CO_2$ concentrations in the grain, DDG, or BSG storage facilities (206 and 207) are monitored via $CO_2$ meters that provide feedback to the grain $CO_2$ terminal (205).

As shown in the example system of FIG. 2, the system includes a Control Center (205). The Control Center includes one or more $CO_2$ pressure regulators, fans, $CO_2$ meters, vaporizers, and satellite or information feeds from grain growing areas The central data collection and decision point is at the main terminal As shown in FIG. 2 $CO_2$ (in liquid or gas form) is ducted into the Control Center (205). If $CO_2$ is sourced in liquid form then it must be processed through the vaporizer at the Control Center that will convert the $CO_2$ liquid into gas. Alternatively, $CO_2$ can be sourced directly from fermentation or thermal energy generation $CO_2$ recovery without the need to be processed through a vaporizer. $CO_2$ streams from both sources can be combined via pressure regulators and flow valves (204). $CO_2$ recovered from ethanol fermentation (201) can be released to a pressure regulator (204). The $CO_2$ gas from this source requires minimal processing and can be released at ambient temperature. The gas then moves through the pressure regulator and is blown with a fan through duct work into either a grain storage facility (206) or a coproduct storage facility (207). The level of $CO_2$ flowing through the pressure regulator and within the storage facilities is regulated by the Control Center (205).

The Control Center regulates the amount of $CO_2$ required based off of feedback received from the storage facilities. The storage facilities can be equipped with $CO_2$ sensors that measure concentration of $CO_2$. Once $CO_2$ reaches desired concentrations between 50 and 70%, the Control Center will switch off the pressure and flow valves, until $CO_2$ is required again. Reduced moisture content is crucial to reducing disease in stored grain. Higher temperatures lead to high prevalence of pests and disease.

Additionally, corn grain storage facilities can have existing aeration ducts that can be used for $CO_2$ treatments. The aeration ducts will be used to distribute $CO_2$ from the pressure regulators and flow valves to the storage facilities. Coproduct storage facilities can be retrofitted with perforated sheet-steel channels in half-shell form laid out on the storage floor. The perforation of the air channels can be adjusted so that the $CO_2$ distributes more equally throughout the grain pile. In addition, the $CO_2$-rich gas stream will be applied from the bottom of the storage facilities to ensure $CO_2$ is penetrating through the grain and allowing moisture to escape through the top of the storage facility. Alternatively, $CO_2$ is applied through the top of the storage facility pushing cool air down through the grain and preventing the top of the grain pile from overheating. Cooling the grain below 70° F. reduces pest infestations.

Data from the $CO_2$ sensors (208) and the $CO_2$ flow meters (204) can be processed in the Control Center (205) to ensure proper $CO_2$ gas concentrations for pest and moisture control treatment. Alternatively, data from the $CO_2$ sensors and the $CO_2$ flow meters can be processed remotely, which may allow for consolidated $CO_2$ control over multiple locations, ease of data access, and time-savings. Remote access to the Control Center (205) ensures constant evaluation of grain storage facility conditions.

The system also integrates data feeds which are processed through the Control Center (205) to make predictions regarding $CO_2$ requirements. Data from agricultural fields is collected from the contiguous United States and accessed through the USDA's National Agricultural Statistics Service (NASS) to make predictions on crop productivity. Data can also be obtained from satellites, which monitor agricultural fields, to make predictions on harvest outputs. This includes information on droughts, floods, vegetation health, growth stages of crops, etc. Crop scouting, which is the process of assessing agricultural pests and diseases, provides additional data points to predict crop performance and assess incoming grain from high pest regions. The combination of data collected from databases, such as the NASS, with satellite data and crop scout analyses, will identify aflatoxin-producing fungi and pest hotspots which in turn will prompt special attention to certain batches of incoming grain and, an upward adjustment in $CO_2$ concentrations for grain storage facilities using the disclosed methods and system. The addition of $CO_2$ will drive grain temperatures down which results in lower pest infestation.

The methods and system disclosed herein constitute a modification and enhancement to the grain receiving and storage area towards the front end of the ethanol production process as well as a modification and enhancement at the backend of the ethanol process where coproducts are dried and stored. The disclosed method, sources $CO_2$ either directly from the fermenters for insect, pest, fungal control or from liquefaction equipment for grain moisture reduction via cooling. Nearby grain storage facilities/grain elevators where $CO_2$ can be shipped by pipeline or truck can also benefit from the disclosed methods and system in their grain treatment. Current methods of drying and pest control have a high energy and financial cost, and are dependent on harmful chemicals for moisture removal and pest control. The disclosed methods and system will reduce the energy input into drying, recycle $CO_2$ that would otherwise be released into the atmosphere, and reduce cost for growers.

Example 2: Cost Reduction and Energy Usage

The methods disclosed herein can significantly reduce the cost and energy for drying grain (Table 1 and Table 2). Grain drying is a significant financial cost for corn growers, as the majority of harvested grain is dried using propane heating, or electric fans, which is an energy cost. Table 1 provides the standards behind the financial savings and life cycle greenhouse gas ("GHG") calculations behind the disclosed method. Life cycle GHG emissions savings are calculated using the US Department of Energy Greenhouse Gases Regulated Emissions and Energy Use in Technologies Model (GREET). Grain drying is currently practiced using aeration via electric fans or heat via propane or natural gas combustion. However, the benefit of the current method and system is the cooling effect of the vaporized liquified $CO_2$. The chilled air acts as a dehumidifier and is gentler on the grain compared to current practices. Table 2 shows the calculations of the potential savings using the disclosed cooling methods versus the traditional heat drying method.

A moisture distribution chart from the Farmers Business Network blog showing the distribution of target moisture content across the United States is used to calculate the average savings of an ethanol plant, if onsite $CO_2$ is used for drying and pest control versus traditional methods. In one example, ethanol plants producing an average of 120 million gallons of ethanol a year, require about 40 million bushels of corn while also producing 300,000 tons of DDG. Ethanol plants will generally accept grain with a maximum 15% moisture content. Based on the moisture distribution chart, and a geographical variation from the Farmers Business Network blog showing grain moisture content across the United States upon harvest, growers or grain elevators delivering to an ethanol plant will on average have to reduce the moisture content by 4%. Using traditional methods of drying, growers or grain elevators delivering to an ethanol plant will spend a combined $10 million annually in aeration and propane costs to meet the total grain demand of the average plant. Using embodiments disclosed herein, a plant introducing grain chilling using onsite compressed $CO_2$ can reduce grain moisture by 1.5% compared to traditional methods of drying thereby saving growers drying costs of $3.84 million. This means that this part of the moisture reduction process for incoming grain with the current method will be performed by the plant instead of the grower. However, ethanol plants will incur $CO_2$ compression cost of $166,000, but receive $60/ton of fermentation $CO_2$ from the government's Inflation Reduction Act (IRA) if the fermentation $CO_2$ is put to new uses. Additional revenues to the plant may be generated from ethanol life cycle carbon intensity reductions if the ethanol is sold in states that have a Low Carbon Fuel Standard (LCFS) such as, for example, California, Washington, and Oregon. Similarly, coproducts which plants dry from 60% moisture to 10% moisture generally using natural gas fired dryers can substitute moisture removal of one to ten percentage points using grain chilling.

Currently, $CO_2$ compression is costly due to the difficulty of capturing $CO_2$ and removing it from surrounding gasses in the air. Therefore, the methods disclosed herein provide a significant reduction in energy usage and cost for drying and treating grain with the additional benefit of cost savings which include using $CO_2$ directly from the fermenters or thermal energy generation, as an ambient gas and releasing directly on the grain for drying or grain pathogen treatment.

Plants implementing embodiments disclosed herein will provide a new use for 12,952 tons (Table 2, $CO_2$ tons needed-annual) of carbon dioxide while offsetting a total of 9,325 tons (Table 2, GHG tons annual) of GHG emissions relative to the traditional cooling and drying methods. Therefore, for every ton of fermentation $CO_2$ that is put to productive use an additional (GHG tons annual×$CO_2$ tons needed-annual) 9,325/12,952=0.72 tons are saved in life cycle GHG emissions.

Table 1 provides the standards behind the financial savings and life cycle greenhouse gas ("GHG") calculations of the proposed method.

| Item | Value | Unit |
|---|---|---|
| Corn Drying Propane Energy Consumption Per 1.5% Moisture Points | 0.03 | gallon/bushel corn |
| Propane Dryer Fans Energy Consumption per 1.5% Moisture Points | 0.015 | kWh/bushel corn |
| Coproduct Drying Natural Gas Energy Consumption Per 3% Moisture Reduction | 0.168 | MMBtu/ton DDG |
| Cost of Propane | 3.20 | $/gallon |
| Cost of Industrial Natural Gas | 7.00 | $/MMBtu |
| Cost of Electricity | 0.16 | $/kWh |
| Carbon Intensity of Propane Combustion | 5,719 | grams GHG/gallon |
| Carbon Intensity of Natural Gas Dryer (adapted from boiler) | 59,379 | grams GHG/MMBtu |
| Carbon Intensity of Per Bushel Per 1.5% Moisture Percentage Reduction | 257 | grams GHG/bushel |
| Carbon Intensity of Electricity Grid Emissions | 0.87 | lbs/kWh |
| $CO_2$ Gas to Liquid Compression Energy | 104 | kWh/ton $CO_2$ |
| Payment under IRA for New Uses of $CO_2$ Gas | $60 | $/ton $CO_2$ |
| Assumed Carbon Price Under Low Carbon Fuel Standard | $80 | $/ton GHG |

Table 2 provides potential cost savings and calculations once the disclosed method is integrated into an ethanol plant.

| Grain Cooling | $CO_2$ Needed (tons) | Compression Cost ($) | GHG (tons) |
|---|---|---|---|
| Corn Treatment | 10,004 | $166,672 | 410 |
| Coproduct Treatment | 2,948 | $49,109 | 121 |
| Totals: | 12,952 | $215,781 | 531 |

| Grain Drying | Thermal Energy (MMBTU) | Fuel Cost Drying ($) | GHG (tons) |
|---|---|---|---|
| Corn Treatment (Propane) | 3,288 | $3,840,000 | 6,863 |
| Coproduct Treatment (Nat Gas) | 50,400 | $352,800 | 2,993 |
| Totals: | 53,688 | $4,192,800 | 9,856 |

Summary: Net Financial Savings

| | |
|---|---|
| Fuel Savings Corn Treatment | $3,673,328 |
| Fuel Savings Coproduct Treatment | $303,691 |
| IRA New $CO_2$ US Payment Corn Treatment | $411,768 |
| IRA New $CO_2$ US Payment Coproduct Treatment | $179,562 |
| LCFS Payments Corn Treatment | $516,212 |
| LCFS Payments Coproduct Treatment | $229,748 |

| Grain Cooling | $CO_2$ Needed (tons) | Compression Cost ($) | GHG (tons) |
|---|---|---|---|
| Total Difference: Grain Drying vs. Cooling | | $5,314,310 | |
| Financial Savings Per Ton Fermentation $CO_2$ | | $410 | |

Summary: GHG Considerations

| | |
|---|---|
| GHG Savings from Fuel Savings (tons) Corn Treatment | 6,453 |
| GHG Savings from Fuel Savings (tons) Coproduct Treatment | 2,872 |
| Total GHG Savings: Green Drying vs. Cooling | 9,325 |
| Ton GHG Savings Per Ton Fermentation $CO_2$ | 0.72 |
| Ethanol Carbon Intensity Reduction (g$CO_2$/MJ) from Corn Treatment | 0.67 |

| | |
|---|---|
| Ethanol Carbon Intensity Reduction (gCO$_2$/MJ) Coproduct Treatment | 0.30 |

All publications, patents, and patent applications mentioned in this specification are herein incorporated by reference to the same extent as if each individual publication, patent, and patent application was specifically and individually indicated to be incorporated by reference.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings the disclosure, and the appended claims. The mere fact that certain measures or features are recited in mutually different dependent claims does not indicate that the combination of these measures or features cannot be used. Any reference signs in the claims should not be construed as limiting the scope.

I claim:

1. A method of drying one or more spent grains in an ethanol plant or alcohol brewery, the method comprising: directing captured $CO_2$ from the ethanol plant or alcohol brewery into a spent grain stored in a grain storage facility, wherein the captured $CO_2$ is a byproduct of alcohol fermentation of a grain at the ethanol plant or alcohol brewery.

2. The method of claim 1, wherein the $CO_2$ is captured $CO_2$ onsite at the ethanol plant or alcohol brewery through the alcohol fermentation of a stored grain.

3. The method of claim 1, wherein the treatment is drying, cooling, disease control, or combinations thereof.

4. The method of claim 1, wherein the captured $CO_2$ is a compressed gas, or a liquid, or provided at ambient temperature.

5. The method of claim 4, wherein the captured $CO_2$ is liquified and is subsequently vaporized before being directed into the spent grains stored in the grain storage facility, drying the spent grains via the $CO_2$ refrigeration cycle.

6. The method of claim 4, wherein the captured $CO_2$ is a liquid or is provided at ambient temperature for drying, cooling, or combinations thereof.

7. The method of claim 1, wherein the grain is corn, dried distillers grains with soluble (DDG), barley, or brewer's spent grain (BSG).

8. The method of claim 1, wherein the treating of spent grain serves to decrease energy use by 50% and reducing grain moisture removal by 1.5% to 15%.

9. The method of claim 8, wherein the treating of spent grain serves to reduce an energy cost to remove grain moisture by up to 90%.

10. The method of claim 8, wherein the use of greenhouse gas (GHG) to remove spent grain moisture is reduced by 90-95%.

11. The method of claim 1, wherein the treating of the one or more spent grains includes a system comprising a control center, one or more ducts, and a $CO_2$ source.

12. The method of claim 11, wherein the control center is connected to a $CO_2$ pressure regulator in communication with the one or more ducts, one or more fans, a $CO_2$ meter, and a vaporizer.

13. The system of claim 1, wherein the spent grain has a 50% reduced curing period.

14. A method comprising:
providing an ethanol plant or alcohol brewery;
providing an alcohol fermentation of a grain facility on site at the ethanol plant or alcohol brewery;
capturing $CO_2$ produced from the alcohol fermentation of thermal energy generation of the grain facility;
providing a spent grain storage facility on site at the ethanol plant or alcohol brewery;
directing the $CO_2$ captured from the alcohol fermentation or thermal energy generation of spent grain facility through spent grain stored in the spent grain storage facility;
wherein the $CO_2$ directed through the spent grain serves to dry the spent grain stored in the spent grain storage facility; and
wherein the $CO_2$ directed through the grain serves to provide disease control of the spent grain stored in the spent grain storage facility.

15. The method of claim 14, wherein the weight of $CO_2$ directed through the spent grain in the grain storage facility to the weight of $CO_2$ emitted by the facility is in the range of 1% to 20%.

16. The system of claim 14, wherein the spent grain has a 50% reduced curing period.

* * * * *